US012059396B2

United States Patent
Splichal

(10) Patent No.: US 12,059,396 B2
(45) Date of Patent: Aug. 13, 2024

(54) METHOD OF MANUFACTURING MECHANORECEPTION STIMULATION FABRIC

(71) Applicant: NABOSO TECHNOLOGY INC., Chandler, AZ (US)

(72) Inventor: Emily Splichal, Chandler, AZ (US)

(73) Assignee: NABOSO TECHNOLOGY INC., Chandler, AZ (US)

( * ) Notice: Subject to any disclaimer, the term of this patent is extended or adjusted under 35 U.S.C. 154(b) by 0 days.

(21) Appl. No.: 17/576,690

(22) Filed: Jan. 14, 2022

(65) Prior Publication Data

US 2022/0133663 A1 May 5, 2022

Related U.S. Application Data

(63) Continuation-in-part of application No. 17/028,774, filed on Sep. 22, 2020, which is a continuation of
(Continued)

(51) Int. Cl.
| | |
|---|---|
| *B29C 41/20* | (2006.01) |
| *A61K 31/19* | (2006.01) |
| *A61K 31/198* | (2006.01) |
| *A61K 31/4174* | (2006.01) |
| *A61K 31/455* | (2006.01) |

(Continued)

(52) U.S. Cl.
CPC ............ *A61K 31/19* (2013.01); *A61K 31/198* (2013.01); *A61K 31/4174* (2013.01); *A61K 31/455* (2013.01); *A61K 31/56* (2013.01); *A61K 31/573* (2013.01); *A61K 31/58* (2013.01); *A61K 33/06* (2013.01); *A61K 33/42* (2013.01); *B29C 33/0022* (2013.01); *B29C 33/3842* (2013.01); *B29C 33/42* (2013.01); *B29C 35/0288* (2013.01); *B29C 35/16* (2013.01); *B29C 41/20* (2013.01); *B29C 41/52* (2013.01); *B29C 65/02* (2013.01); *B29D 99/0064* (2013.01); *B29K 2027/06* (2013.01); *B29K 2995/0074* (2013.01); *B29L 2031/48* (2013.01)

(58) Field of Classification Search
CPC .............................. B29C 70/78; B29C 70/747
See application file for complete search history.

(56) References Cited

U.S. PATENT DOCUMENTS

| | | | | |
|---|---|---|---|---|
| 4,151,660 A | * | 5/1979 | Yoshimi ................. | A43B 17/04 36/44 |
| 6,247,999 B1 | * | 6/2001 | Tokiwa ................. | B24B 41/005 483/33 |

(Continued)

*Primary Examiner* — Scott W Dodds
(74) *Attorney, Agent, or Firm* — Womble Bond Dickinson (US) LLP

(57) ABSTRACT

A method for manufacturing the mechanoreception fabric for incorporation into a garment or item of apparel sets a liquid substrate to a fabric weave to produce a plurality of protuberances in graticulate array and spaced apart across a surface of the fabric. The plurality of protuberances includes pyramidal nodes, each independent and separate from other nodes, not less than 1 mm apart at the base and not more than 5 mm apart at each apex and 1.5 mm in height. Because the nodes are separated and not in contact with each other, the fabric produced is still stretchable and wearable when incorporated into an item of apparel despite the nodes having a hardness of between Shore A 60 and 80.

17 Claims, 1 Drawing Sheet

Related U.S. Application Data application No. 15/441,553, filed on Feb. 24, 2017, now abandoned.

(51) Int. Cl.

| | | |
|---|---|---|
| *A61K 31/56* | (2006.01) | |
| *A61K 31/573* | (2006.01) | |
| *A61K 31/58* | (2006.01) | |
| *A61K 33/06* | (2006.01) | |
| *A61K 33/42* | (2006.01) | |
| *B29C 33/00* | (2006.01) | |
| *B29C 33/38* | (2006.01) | |
| *B29C 33/42* | (2006.01) | |
| *B29C 35/02* | (2006.01) | |
| *B29C 35/16* | (2006.01) | |
| *B29C 41/52* | (2006.01) | |
| *B29C 65/02* | (2006.01) | |
| *B29D 99/00* | (2010.01) | |
| *B29K 27/06* | (2006.01) | |
| *B29L 31/48* | (2006.01) | |

(56) References Cited

U.S. PATENT DOCUMENTS

| | | | |
|---|---|---|---|
| 2015/0218750 A1* | 8/2015 | Lesser | B29C 66/472 |
| | | | 428/161 |
| 2016/0287472 A1* | 10/2016 | Starzhynskaya | A61H 39/04 |
| 2021/0000686 A1* | 1/2021 | Splichal | A61H 39/00 |

* cited by examiner

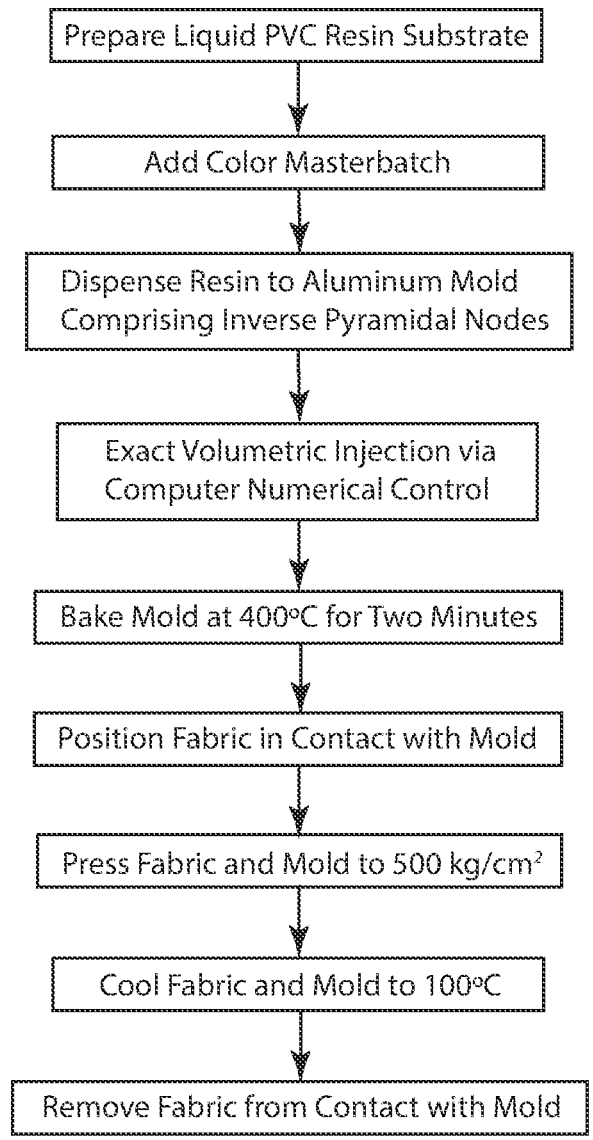

METHOD OF MANUFACTURING MECHANORECEPTION STIMULATION FABRIC

BACKGROUND OF THE INVENTION

Somatosensory input from the lower limb has long been recognized as an important source of sensory information in controlling standing and balance. E.g. Paul M. Kennedy and Timothy Inglis, *Distribution and Behavior of Glabrous Cutaneous Receptors in the Human Foot Sole*, Journal of Physiology, 538.3, 995-1002 (2002). In regulating proprioception, cutaneous receptors in the sole of the foot are sensitive to contact pressures and may be sensitive to potential changes in distribution of pressures across receptive fields. Id. at 995.

Afferent signals from the small nerves in the plantar surface of the foot, therefore, are known to assist in balance and posture, reducing sway and regulating stride. E.g. Li Li et al., *The Contribution of Small and Large Sensory Afferents to Postural Control in Patients with Peripheral Neuropathy*, Journal of Sport and Health Science, 8, 218-227 (2019). Further, active control by nervous regulation of skeletal muscle is responsible for sway detection and postural correction. Id., 220. The functional role of the nervous system in "active control"; that is, the nervous regulation of skeletal muscle that requires energy expenditure in maintaining balance and posture; may be subdivided into four components: stimulation collection via sensory receptors, afferent signaling via sensory neurons, central nervous system ("CNS") control of information processing and decision making in the CNS, and efferent signaling to skeletal muscles via α-moto-neurons. Id.

Plantar cutaneous feedback, then, from the cutaneous receptors in the soles of the feet, help regulate postural sway and maintain balance. Id. See also Anna L. Hatton et al., *Altering Gait by Way of Stimulation of the Plantar Surface of the Foot: The Immediate Effect of Wearing Textured Insoles in Older Fallers*, Journal of Foot and Ankle Research, 5, Article No. 11 (2012). Similarly, it is believed that receptors in the hands may increase profusion pressure and blood flow to the extremity, thereby heightening perception, dexterity, and prehensility.

Providing a means of stimulating the receptor fields on a user's hands and feet during stretching, for example, or stimulating the plantar receptive fields specifically when walking or standing, may greatly assist a user in walking, running, standing, and in maintaining balance and posture. Further, providing a surface material with a means of effectuating an increase in stimulation of targeted receptive fields in the user's hands and feet in proportion to the pressure applied in contact with the surface may increase stimulation in proportion with the amount of weight or force applied by the user, and thereby increasingly affect the user's balance and posture when running, for example, or when applying more weight to a particular limb, as when stretching during calisthenics, or when standing or striding on one foot, for example. Increasing stimulation of receptive fields in proportion to pressure applied in contact with the surface, therefore, may increase neuronal feedback to reflexively increase effective balance and posture and positively impact ambulation and rehabilitation in users with peripheral neuropathy as well as assist healthy users attain optimal performance.

Wheat et al. describe effects of textured socks on balance control. See "Effects of Textured Socks on Balance and Control During Single-Leg Standing in Healthy Adults," *Procedia Engineering* 72 (2014) 120-125. Prototype socks were made with nodules of 5 mm diameter that were sewn onto the sock on the plantar surface, the dorsal surface, sides of the foot, and covering the entire surface. The nodules used were craft pom-poms, sewn to the outside of the sock approximately 200 mm apart, and had relatively large diameters of 5 mm, 10 mm, and 12 mm. Id., 121.

Further, it is contemplated that increasing blood flow and perfusion pressure to the regions of the body resulting from the afferent signaling from the receptive fields may assist in rehabilitation, sensory perception, relief from symptoms of inflammation (such as arthritis, for example) and enable increased dexterity in use of the limb or extremity.

The present invention, therefore, relates to a mechanoreception stimulation garment devised to maximize mechanoreception when worn. The present invention relates to a wearable fabric item of apparel that includes an interior surface whereupon a plurality of protuberances is disposed. The interior surface therefore maintains contact with a user's glabrous innervate skin (or, in some embodiments, the hairy skin) when the garment or item of apparel is worn. Elastomeric properties of the garment may increase or force contact of the plurality of protuberances with the user's skin. Contradistinct the garments employed by Wheat et al. in their study, here the plurality of protuberances comprises a plurality of pyramidal, relatively hard (Shore A 75 in an example embodiment), polymeric structures, approximately 1.5 mm in height and with bases 2.5 mm$^2$. The bases are spaced apart not less than 1 mm and the apices are spaced apart no more than 5 mm. In a preferred embodiment configured to maximize mechanoreception from stimulation of targeted receptive fields, the apices of the nodes are spaced 3.5 mm apart. This particular grouping and arrangement of protuberances, each having an acuate apex for focused impression into the targeted receptive fields, is contemplated to maximize proprioception and skin perfusion pressure when forced in contact with the wearer's skin.

The garment, in all embodiments, therefore maintains stimulation of the receptive fields of a user's skin when worn by the wearer, and may assist in proprioception, balance and posture when walking or standing, increasing blood flow to the glabrous skin, increasing perfusion pressure at the extremities, as well as increasing awareness and perception of the limb and the limb's position and orientation.

FIELD OF THE INVENTION

The present invention relates to a method of manufacturing the mechanoreception stimulation fabric that has a plurality of relatively small polymeric, pyramidal protuberances affixed to an interior surface of the fabric. Each of the pyramidal protuberances is dispensed into a mold to certain specifications and fused to a surface of the fabric at heat and pressure. Each node is durably affixed to the fabric to ensure longevity of use. A minimum distance of 1 mm is maintained between each node's base (the nodes do not touch), and a maximum distance of not more than 5 mm between each apex is also maintained, whereby the fabric is enabled to stretch and flex in a similar capacity as before the protuberances were affixed to the fabric.

The fabric is then usable in a garment or item of apparel to effectuate contact with specific areas of the wearer's skin and stimulate mechanoreception via targeted receptive fields. The garment or item of apparel ultimately produced, then, is configured to stimulate the receptive fields of the wearers glabrous innervate skin to positively affect the user's balance and posture when standing and walking. By maintaining pressured contact against the wearer's skin, the mechanoreception stimulation fabric increases perception of the wearer's extremities as well as skin perfusion pressure to lessen fatigue of the feet (when wearing the garment as a sock) and hands (when wearing the garment as a glove) and may assist in overall awareness of the limb's position and orientation.

SUMMARY OF THE INVENTION

The present method for manufacturing the mechanoreception stimulation fabric has been devised to enable affixing a plurality of protuberances comprising a plurality of relatively small, closely spaced, but individually separate nodes to a fabric for incorporation into a garment or item of apparel. The garment or apparel, when worn, is devised to increase blood flow, perfusion pressure and, where worn on the user's feet, to increase balance and lessen falls by targeted stimulation to the receptive fields in a wearer's innervate skin.

Each node is configured to be hard enough for stimulation of the user's skin (at Shore A 75, for example), while being individually affixed to the fabric to allow for flexibility and stretchability of the fabric in normal use and durability of the nodes and reuse of the fabric over time. The nodes must be shaped appropriately, presenting an apex and square base affixed to the fabric, each individually spaced in close proximity upon the fabric weave.

In an example embodiment contemplated herein, the plurality of protuberances includes polymeric nodes that have a hardness in the range of Shore A 65 to 80. In a preferred embodiment disclosed herein, the hardness of each node is Shore A 75. Each of these nodes includes a base which is affixed to the fabric, which fabric is yet stretchable and devised for wear as a garment or an item of apparel. The nodes are arranged in a graticulate array across an interior surface of the final garment or apparel and are spaced apart and sized appropriately for directed contact with targeted areas of the wearer's skin in such a way as not to interfere with the general wearability and functionality of the garment or item of apparel.

The plurality of protuberances devised herein is contemplated to be specifically sized and spaced apart with intent to maximize mechanoreception of the wearer. In an example embodiment contemplated herein, each of the plurality of protuberances is a pyramidal node, approximately 1.5 in height with a base of 2.5 mm² (that is, 2.5 mm along each side). Each node is approximately 65 to 80 Shore A hardness (with a preferred hardness of 75 Shore A in at least one embodiment). The fabric may be incorporated into garments or items of apparel to target specific receptive fields. However, each grouping of nodes is contemplated to be not less than 1 mm apart at the base and no more than 5 mm apart at each apex, thereby confining the specific arrangement of nodes into a graticulate field that superimposes over a targeted receptive field in a wearer's glabrous innervate skin. In a preferred embodiment disclosed herein, the apices of the nodes are 3.5 mm apart.

The garments set forth herein, whereupon the plurality of protuberances is affixed across an interior surface, are contemplated to be socks, gloves, sweatbands, and any other item of apparel wearable upon a person in contact with the innervate skin in the hands, feet, limbs, and forehead, for example. Additionally, the fabric rendered by the instant method may be used to present surfaces on other items, such as upholstery or sleeves for objects and handles. The elastomeric properties of some fabrics may increase the pressure of the protuberances' contact with the innervate skin when the fabric is incorporated into apparel.

The particular shape of the pyramidal nodes is deemed important. The shape is devised to increase stimulation proportionately with pressure applied. Each apex of each node is relatively acute. Increasing pressured contact therewith pushes the node to stretch the user's skin upon and over the sides of the node. As the node slopes outwardly toward the base, so the area of skin subject to contact and stimulation is increased. This increasing stimulation proportionate to pressure applied is termed a "focus" herein throughout/ The concept contemplates that each node stimulates a focus within the receptive field to increased afferent signaling in proportion to pressure applied. Each focus, therefore, is believed to increase mechanoreception and thus aid in balance and in reducing sway in embodiments used in connection with the receptive fields of a user's feet and generally to increase perfusion pressure and blood flow, lessen fatigue, and increase user perception and awareness of the extremity with which the instant fabric is used. The molding employed in this method of manufacture is devised to render these characteristics and structure to the nodes and affix such structures to a fabric weave.

The method employed to affix the nodes to the fabric includes taking a liquid polymer substrate, such as Poly Vinyl Chloride ("PVC") for example and, in some embodiments, adding a color masterbatch to color the nodes for visual apprehension. A mold may be prepared in an aluminum alloy. The mold is shaped appropriate for the final garment or apparel the fabric will be incorporated into, and typically embodies an obround, or rectangular parallelepiped, into a surface of which is disposed a plurality of inverse pyramidal receptacles, each spaced apart 1 mm across the surface of the mold. The liquid substrate is then precisely dispensed across the mold surface by means of a Computer Numerical Control ("CNC") dispensing machine, whereby precise volumes of the liquid substrate are dispensed to precisely fill each receptacle without the substrate overflowing or bleeding across the surface of the mold. Each receptacle therefore contains a specific volume of the substrate and presents a flat liquid layer congruent with the mold's surface, which liquid surface is presented for contact with the fabric when the fabric is placed over or upon the mold.

Once dispensation of the substrate is complete, the mold with substrate is passed through a baking line at approximately 400° C. for two minutes. The temperature and time is calculated to cause the surface of the mold to reach a specific setting temperature. Once temperature is attained, a fabric blank; or, where the method is employed in the manufacture of socks, the sock inside-out; is placed upon a positioning plate, to maintain the fabric in the desired position upon the mold, and then the fabric is placed in direct contact with the mold such that the desired surface of the fabric is caused to overlie the mold surface and contact the liquid substrate. The mold and fabric are then placed into a hydraulic press and pressed to a set pressure, typically 500 kg/cm². The mold and fabric are thence removed and cooled to approximately 100° C. Once cooled, the positioning plate is removed and the fabric is peeled from the mold.

The plurality of protuberances now solidified and hardened, is affixed to the fabric in like pattern as captured by the mold, with each node separate and distinct, at least 1 mm apart between the bases and not more than 5 mm apart at the apices. In a preferred embodiment, the apices are 3.5 mm apart. The fabric may now be incorporated into a garment or, where socks are produced, turned right side out and paired for packaging.

Thus has been broadly outlined the general steps informing the method of manufacture of the mechanoreception stimulation fabric so that the detailed description thereof that follows may be better understood and in order that the present contribution to the art may be better appreciated.

BRIEF DESCRIPTION OF THE DRAWINGS

Figures

FIG. 1 is a flow diagram setting forth exemplary steps of the instant method.

DETAILED DESCRIPTION OF THE DRAWINGS

An example embodiment of the instant method of manufacture of the mechanoreception stimulation fabric is set forth in FIG. 1. A plurality of protuberances, consisting of a plurality of pyramidal nodes, is affixed to a fabric weave of a garment or blank for use as apparel. The exemplary steps as set forth and depicted herein are intended to illustrate an example embodiment of the instant method only, and, in and of themselves, are not intended to be limiting but are provided to breathe life into the accompanying claims.

Referring now to FIG. 1, a polyvinyl chloride ("PVC") resin is prepared as a liquid substrate for incorporation into a Computer Numerical Control ("CNC") machine. In the example method set forth herein, color is added to the substrate by addition of a color masterbatch. The colored substrate is then added to the CNC for precise volumetric dispensation interior to a mold.

In the example embodiment set forth herein, a mold is presented for receipt of the substrate, said mold rendered in aluminum and having a plurality of pyramid-shaped cavities pressed, scored, or molded into an upper surface thereof. Each of the pyramid-shaped cavities is 2.5 by 2.5 mm at each opening at the upper surface, converging to an acuate apex 1.5 mm deep along a vertical axis into the mold, and spaced 1 mm apart across the upper surface of the mold. Use of the CNC ensures precise volumetric dispensation of the substrate to fill each pyramid-shaped cavity to a volume wherein a surface of the substrate is generally congruent with the upper surface of the mold. Surface tension of the liquid substrate may allow for precise volumetric dispensation to slightly overfill each inverted pyramid, to produce a surface of the injected substrate that is slightly above the upper surface of the mold in some capacity. In either case, however, the substrate is maintained in discrete positions corresponding to the position of each of the pyramid-shaped cavities in conformity with the pyramid shape whereby a square base is fashioned affixed to the fabric.

The mold itself may be shaped specifically for use with particular fabric blanks for which certain items of apparel are contemplated. For example, a generally oval or obround mold may be configured for use in creating socks. Or the mold may be arranged for creation of a glove, say. Alternatively, the mold may be a parallelepiped or other shaped expanse used for pressing blanks from which multiple and varied items of apparel may be derived. Where the method is used to produce socks, a premade sock may be turned inside-out and inverted and fitted to the mold such that the interior surface of the sock sole is caused to overlie and directly contact the mold.

Once the substrate has been properly dispensed to fill each of the inverted pyramidal cavities, the mold is baked for two minutes at 400° C. Once removed from the heat, the fabric blank is positioned in contact with the mold in such a manner to accommodate the desired placement of the plurality of protuberances when affixed to the fabric at completion of the present method. The fabric and mold are then subjected to pressure and pressed at 500 kg/cm². After pressing, the mold is cooled to 100° C. and thereafter the fabric is separated from the mold. The substrate is solidified and affixed to the fabric presenting a plurality of protuberances consisting of a plurality of pyramidal nodes, each 1.5 mm in height, with a square base dimensioned 2.5 mm by 2.5 mm. Each node is spaced not less than 1 mm between the bases and not more than 5 mm between each apex. In a preferred embodiment disclosed herein, each node has a hardness of Shore A 60 to 80, with a preferred hardness of 75.

Each node is affixed to the fabric without appreciably impeding the stretchability or wearability of the fabric. Where the fabric produced is a blank, the blank may be used in the production of a garment or apparel. Where the fabric produced is a sock, the sock is prepared for packaging and distribution.

What is claimed is:

1. A method of manufacturing a mechanoreception stimulation garment or item of apparel for wearing by a user comprising:

cutting a mold plate to a shape appropriate for use in molding an arrangement of a plurality of protuberances upon an interior surface of a garment or item of apparel;

scoring the mold plate to include a plurality of inverse pyramidal nodes upon a surface thereof, said nodes arranged in an array corresponding to the position of the plurality of protuberances;

dispensing controlled volumes of liquid polymer or liquid substrate into the inverse pyramidal nodes in the mold plate such that the surface of the liquid polymer or liquid substrate is congruent with the surface of the mold plate without overflowing;

heating the mold plate so that the surface of the liquid polymer or liquid substrate reaches a set temperature;

placing a fabric upon a positioning plate corresponding to the shape of the mold plate such that a surface of the fabric contacts a surface of the mold plate wherein the liquid polymer or liquid substrate is housed;

subjecting the fabric in contact with the mold plate to press at a target pressure;

cooling the fabric and mold plate so that the mold temperature falls to a desired cooling temperature; and peeling the fabric from the mold plate after the mold plate has cooled to the desired cooling temperature;

wherein the plurality of protuberances is affixed to the surface of the fabric, each node independent, separate from, and not in contact with any adjacent node, whereby the fabric is stretchable; and forming the garment or item of apparel from the fabric, wherein the plurality of protuberances is upon the interior surface of the garment or item of apparel and configured to contact the innervate skin of the user when the user wears the garment or item of apparel.

2. The method of manufacturing the mechanoreception stimulation garment or item of apparel of claim 1 wherein the liquid polymer or liquid substrate has a Shore A hardness of between 60 and 80 when solidified and affixed to the fabric.

3. The method of manufacturing the mechanoreception stimulation garment or item of apparel of claim 2 wherein each node is 1.5 mm in height and 2.5 mm by 2.5 mm in length and width at the base.

4. The method of manufacturing the mechanoreception stimulation garment or item of apparel of claim 3 further comprising adding color to the liquid polymer or liquid substrate previous to dispensing into the mold plate.

5. The method of manufacturing the mechanoreception stimulation garment or item of apparel of claim 4 wherein the liquid polymer or liquid substrate is polyvinyl chloride.

6. The method of manufacturing the mechanoreception stimulation garment or item of apparel of claim 5 wherein dispensing controlled volumes of the liquid polymer or liquid substrate into the mold plate is accomplished by a Computer Numeric Control dispensing machine whereby precise volumes of the polymer or liquid substrate are dispensed into the mold plate.

7. The method of manufacturing the mechanoreception stimulation garment or item of apparel of claim 6 wherein said heating occurs for at least two minutes.

8. The method of manufacturing the mechanoreception stimulation garment or item of apparel of claim 6 wherein the set temperature is about 400° C.

9. The method of manufacturing the mechanoreception stimulation garment or item of apparel of claim 8 wherein the desired cooling temperature is about 100° C.

10. The method of manufacturing the mechanoreception stimulation garment or item of apparel of claim 8 wherein the target pressure is about 500 kg/cm$^2$.

11. The method of manufacturing the mechanoreception stimulation garment or item of apparel of claim 1, wherein the garment or item of apparel is a sock.

12. A method of manufacturing a mechanoreception stimulation garment or item of apparel for wearing by a user comprising:
   cutting a mold plate to a shape appropriate for use in molding an arrangement of a plurality of protuberances upon an interior surface of a garment or item of apparel;
   scoring the mold plate to include a plurality of inverse pyramidal nodes upon a surface thereof, said pyramidal nodes being 2.5 mm by 2.5 mm at the opening at the surface of the mold, not more than 1.5 mm deep, and not more than 1 mm apart, said nodes arranged in a graticulate array corresponding to the position of the plurality of protuberances upon a garment or item of apparel;
   dispensing controlled volumes of liquid polymer or liquid substrate into the inverse pyramidal nodes in the mold plate such that the surface of the liquid polymer or liquid substrate is congruent with the surface of the mold plate without overflowing;
   heating the mold plate to approximately 400° C. for at least two minutes such that the surface of the liquid polymer or liquid substrate reaches a specific set temperature;
   placing fabric upon a positioning plate corresponding to the shape of the mold plate such that a surface of the fabric contacts a surface of the mold plate wherein the liquid polymer or liquid substrate is housed;
   subjecting the fabric in contact with the mold plate to a pressure of about 500 kg/cm$^2$, cooling the fabric and mold plate so that the mold plate temperature falls to approximately 100° C.; and
   peeling the fabric from the mold plate after the mold plate has cooled;
   wherein the plurality of protuberances is affixed to the interior surface of the fabric and arranged not more than 1 mm apart at each base and not more than 5 mm apart at each apex, and wherein each node is independent, separate from, and not in contact with any adjacent node, whereby the fabric is stretchable; and
   forming the garment or item of apparel from the fabric, wherein the plurality of protuberances is upon the interior surface of the garment or item of apparel and configured to contact the innervate skin of the user when the user wears the garment or item of apparel.

13. The method of manufacturing the mechanoreception stimulation garment or item of apparel of claim 12 wherein the liquid polymer or substrate has a Shore A hardness of between 60 and 80 when solidified and affixed to the fabric.

14. The method of manufacturing the mechanoreception stimulation garment or item of apparel of claim 13 wherein the liquid polymer or substrate is polyvinyl chloride.

15. The method of manufacturing the mechanoreception stimulation garment or item of apparel of claim 14 further comprising adding color to the liquid polymer or substrate previous to dispensing into the mold plate.

16. The method of manufacturing the mechanoreception stimulation garment or item of apparel of claim 15 wherein dispensing controlled volumes of the liquid polymer or substrate into the mold plate is accomplished by a Computer Numeric Control dispensing machine whereby precise volumes of the polymer or substrate are dispensed into the mold plate.

17. The method of manufacturing the mechanoreception stimulation garment or item of apparel of claim 12, wherein the garment or item of apparel is a sock.

* * * * *